United States Patent [19]

Moroni

[11] Patent Number: 4,613,596
[45] Date of Patent: Sep. 23, 1986

[54] AMINO METHYL FURANS AND PHARMACEUTICAL COMPOSITIONS

[75] Inventor: Adolfo Moroni, Brescia, Italy

[73] Assignee: Magis Farmaceutrici s.r.l., Brescia, Italy

[21] Appl. No.: 808,375

[22] Filed: Dec. 16, 1985

Related U.S. Application Data

[63] Continuation of Ser. No. 536,730, Sep. 28, 1983, abandoned.

[30] Foreign Application Priority Data

Apr. 27, 1982 [IT] Italy ................. 20954 A/82

[51] Int. Cl.⁴ .............. A61K 31/445; A61K 31/40; C07D 405/12
[52] U.S. Cl. .................. 514/210; 514/212; 514/326; 514/422; 514/471; 546/214; 548/517; 548/961; 548/962; 544/152; 544/379; 549/492; 540/596
[58] Field of Search ........... 546/214; 548/517; 260/330.9; 514/210, 212, 326, 422, 471

[56] References Cited

U.S. PATENT DOCUMENTS

| | | | |
|---|---|---|---|
| 4,233,302 | 11/1980 | Martin-Smith | 549/492 |
| 4,279,911 | 7/1981 | Martin-Smith et al. | 424/251 |
| 4,304,780 | 12/1981 | Martin-Smith et al. | 424/263 |
| 4,426,521 | 1/1984 | Tanaka | 549/492 |
| 4,427,685 | 1/1984 | Stemp | 549/492 |

*Primary Examiner*—Robert W. Ramsuer
*Attorney, Agent, or Firm*—Stevens, Davis, Miller & Mosher

[57] ABSTRACT

New compounds active in the treatment of ulcers and alergic skin symptoms are prepared by reacting 2-[[5-[(dimethylamino)methyl]furfuryl]thio]ethylmethylsulphide with a suitable compound of formula RH. Said compounds are particularly useful as active principles in pharmaceutical compositions for use in the treatment of affections which require the administration of antagonists for histamine $H_2$ receptors.

18 Claims, No Drawings

AMINO METHYL FURANS AND PHARMACEUTICAL COMPOSITIONS

This application is a continuation of application Ser. No. 536,730, filed Sept. 28, 1983, abandoned.

The present invention relates to new compounds with antiulcerative activity, the process for their preparation, and the pharmaceutical compositions which contain them.

More particularly, the present invention relates to new compounds of formula (I)

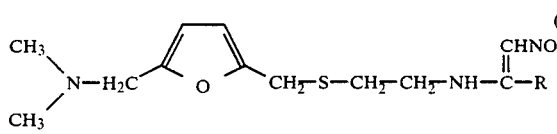

in which R is a piperidino, 4-methylpiperidino, (3-N-ethylpiperidinyl)-amino, 4-(2-hydroxyethyl)-1-piperazino, 4-benzyl-piperidino, 4-benzyl-piperazino, ethyleneimino, cyclopropyleneimino, cyclohexylamino, 1,4-cyclohexadienylamino, 1,4-cyclohexadienyl-2-methylamino, 1,4-cyclohexadienyl-2-ethylamino, hexamethyleneimino, (N-hexamethyleneimino)-amino, cycloheptylamino, cyclopentylamino, pyrrolidino, morpholino, endo-2-norbornylamino, or norbornen-2-ylamino, and their pharmaceutically acceptable salts.

The pharmaceutically acceptable salts comprise for example both non-toxic salts obtained by adding inorganic acids such as hydrochloric, hydrobromic, hydroiodic, phosphoric or sulphuric acid, and non-toxic salts obtained by adding organic acids such as maleic, acetic, citric, oxalic, succinic, benzoic, tartaric, fumaric, mandelic, ascorbic, methylsulphonic or ethylsulphonic acid.

The present invention also relates to a new process for preparing compounds of formula (I) as heretofore defined, and their pharmaceutically acceptable salts, characterised by reacting the compound of formula (III)

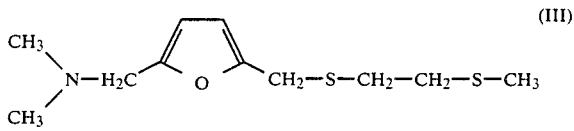

with a compound of formula (II)

$$\overset{CHNO_2}{\underset{NH_2-C-R}{\|}} \quad (II)$$

in which R is as heretofore defined, at a temperature of 80° C., then isolating the compound obtained and, optionally, salifying it.

The compounds of formula (I) as heretofore defined, and their pharmaceutically acceptable salts, have proved useful in the treatment of affections requiring the administration of antagonists for receptors of histamine H$_2$, such as the peptic ulcer or allergic skin symptoms. Thus the present invention further relates to pharmaceutical compounds characterised by containing as their active principle an effective quantity of one or more compounds of formula (I) as heretofore defined, or their pharmaceutically acceptable salts, either as such or in union with other compatible active principles and/or with vehicles, diluents, solvents and/or pharmaceutically acceptable excipients.

Table A given hereinafter contains, together with the meanings of R as heretofore defined, the corresponding structural formula of R and the symbol by which the corresponding compound of formula (I) is known hereinafter for brevity.

TABLE A

| Group R | | symbol of corresponding compound of formula (I) |
|---|---|---|
| Structural formula | Name | |
|  | piperidino | AU/001 |
|  | 4-methyl-piperidino | AU/002 |
|  | (3-N—ethyl-piperidinyl) amino | AU/003 |
|  | 4-(2-hydroxy-ethyl)-1-piperazino | AU/004 |
|  | 4-benzyl-piperidino | AU/005 |
|  | 4-benzyl-1-piperazino | AU/006 |
|  | ethyleneimino | AU/007 |
|  | cyclopropyleneimino | AU/008 |
|  | cyclohexylamino | AU/009 |
|  | 1,4-cyclohexadienyl-amino | AU/010 |
|  | 1,4-cyclohexadienyl-2-methylamino | AU/011 |

TABLE A-continued

| Group R | | symbol of corresponding compound of formula (I) |
|---|---|---|
| Structural formula | Name | |
| ⌬—CH₂—CH₂—NH— | 1,4-cyclo-hexadienyl-2-ethylamino | AU/012 |
| CH₂—CH₂—N— / CH₂ \ CH₂—CH₂—CH₂ | hexamethyleneimino | AU/013 |
| CH₂—CH₂—N—NH / CH₂ \ CH₂—CH₂—CH₂ | N—amino-hexamethyleneimino | AU/014 |
| CH₂—CH₂—CH₂NH / CH₂ \ CH₂—CH₂—CH₂ | cycloheptylamino | AU/015 |
| CH₂—CH₂ \ CH—NH / CH₂—CH₂ | cyclopentylamino | AU/106 |
| CH₂—CH₂ \ N— / CH₂—CH₂ | pyrrolidino | AU/017 |
| CH₂—CH₂ / \ O N— \ / CH₂—CH₂ | morpholino | AU/018 |
| bicyclic-CH₂-NH | endo-2-norbornylamino | AU/019 |
| bicyclic-CH₂-NH | norbornen-2-yl-amino | AU/020 |
| | norbornen-2-yl-amino | AU/020 |

The compounds of formula (I) and their pharmaceutically acceptable salts are active in the treatment of affections requiring the administration of receptors of histamine $H_2$, such as the peptic ulcer or allergic skin symptoms. For example, they have an antiulcerative activity which exceeds that of ranitidine or cimetidine, which are active principles already known in the art. In particular, they have an activity which is 1.1 to 1.3 times greater than ranitidine and 5 to 10 times greater than cimetidine. Moreover, the compounds of formula (I) and their pharmaceutically acceptable salts offer the practical absence of side-effects. Said characteristics of high activity and practical absence of side-effects have been evaluated by studying the acute toxicity, subchronic toxicity, chronic toxicity, fetal toxicity and cardiocirculatory effects on ulcers deriving from ligature of the pylorus and retention, on gastric secretion and on gastric hyperacidity deriving from tetragastrin.

Acute toxicity was studied in male and female mice of Swiss stock, and in male and female albino rats of Wistar stock, by administering the active principle orally, intravenously and intramuscularly.

For each method of administration, doses in geometrical progression were administered to 10 animals for each dose over a period of observation of 10 days.

On termination of the period of observation, the $LD_{50}$ and the relative reliability limits were calculated by the method of Litchfield and Wilcoxon (Pharmacol. Exp. Ther., 96-19, 1949).

The results are shown in Table 1.

TABLE 1

| $LD_{50}$ (rel. lim. 95) mg/kg | Mouse | | | Rat | | |
|---|---|---|---|---|---|---|
| | Oral admin. | Intrav. admin. | Intram. admin. | Oral admin. | Intrav. admin. | Intram. admin. |
| AU/001 | 2600 | 90 | 300 | 5520∅ | 100 | 2100 |
| AU/002 | 2700 | 100 | 320 | 5520∅ | 100 | 2000 |
| AU/003 | 2800 | 90 | 300 | 5550∅ | 100 | 2200 |
| AU/004 | 2700 | 95 | 300 | 5550∅ | 110 | 2000 |
| AU/005 | 2700 | 95 | 300 | 5500∅ | 110 | 2100 |
| AU/006 | 2700 | 90 | 300 | 5550∅ | 100 | 2100 |
| AU/007 | 2800 | 100 | 310 | 5550∅ | 100 | 2100 |
| AU/008 | 2600 | 100 | 310 | 5550∅ | 100 | 2200 |
| AU/009 | 2600 | 100 | 300 | 5550∅ | 110 | 2200 |
| AU/010 | 2700 | 95 | 310 | 5501∅ | 110 | 2200 |
| AU/011 | 2700 | 90 | 310 | 5510∅ | 110 | 2100 |
| AU/012 | 2800 | 90 | 300 | 5520∅ | 110 | 2100 |
| AU/013 | 2700 | 90 | 300 | 5530∅ | 100 | 2100 |
| AU/014 | 2600 | 90 | 300 | 5550∅ | 100 | 2200 |
| AU/015 | 2800 | 100 | 300 | 5550∅ | 100 | 2200 |
| AU/016 | 2700 | 90 | 300 | 5501∅ | 100 | 2200 |
| AU/017 | 2600 | 100 | 300 | 5520∅ | 100 | 2200 |
| AU/018 | 2700 | 90 | 350 | 5520∅ | 100 | 2200 |
| AU/019 | 2600 | 100 | 300 | 5520∅ | 120 | 2100 |
| AU/020 | 2700 | 110 | 300 | 5550∅ | 110 | 2100 |

The subchronic toxicity test was carried out for each examined compound on 100 albino rats (Sprague-Dawley stock, 50 males and 50 females) having an average weight of about 120 grams.

The rats, maintained under standard environmental and diet conditions, were divided into 4 groups of 25 animals each, to which the dose given in Table 2 was administered intravenously (daily seven times per week for a treatment period of 4 weeks).

TABLE 2

| | |
|---|---|
| 1st group: | controls (physiological solution) |
| 2nd group: | AU/001-002-003-004-005-006-007-008-009-010-011-012-013-014-015-016-017-018-019-020 (1 mg/kg) |
| 3rd group: | AU/001-002-003-004-005-006-007-008-009-010-011-012-013-014-015-016-017-018-019-020 (5 mg/kg) |
| 4th group: | AU/001-002-003-004-005-006-007-008-009-010-011-012-013-014-015-016-017-018-019-020 (10 mg/kg) |

For each examined product, the test was also carried out on 10 adult dogs, 5 males and 5 females of Beagle breed having a weight of approximately 10 kg.

The dogs, maintained under standard environmental and diet conditions, were divided into 2 groups of 5 animals each, the first group (controls) being administered with a physiological solution over 4 weeks at a frequency of 7 times per week, and the second group being administered with the compounds AU/001-002-003-004-005-006-007-008-009-010-011-012-013-014-015-016-017-018-019-020 at a dose of 5 mg/kg, likewise over 4 weeks at a frequency of 7 times per week.

The condition of the rats and dogs remained excellent, both in the case of the control animals and in the case of those treated with the products examined.

Hematological, hematochemical, urine and hematopathological examinations remained within the norm. No variation occurred which could be imputed to the treatment effected with the aforesaid doses.

For each examined compound, the chronic toxicity test was carried out on 60 albino rats of Sprague-Dawley stock, of both sexes, having an average weight of 97±5 grams, and on 10 Beagle dogs of both sexes having an average weight of 10 kg.

The treatment for the rats and dogs was effected orally (gastric probe for the rats) 7 times per week for 24 weeks with equal doses of all compounds from AU/001 to AU/020, as described in Table A, said doses being shown in Table 3.

TABLE 3

| Animal | Method of administration | Dose of preferred compounds |
| --- | --- | --- |
| Rat (1st group) | Gastric probe | Vehicle |
| Rat (2nd group) | " | 25 mg/kg |
| Rat (3rd group) | " | 50 mg/kg |
| Rat (4th group) | " | 100 mg/kg |
| Dog (1st group) | In daily diet | no treatment |
| Dog (2nd group) | " | 25 mg/kg |
| Dog (3rd group) | " | 50 mg/kg |
| Dog (4th group) | " | 100 mg/kg |

The daily oral administration of the examined compounds to the rat or dog produced no change in the hematological, hematochemical or urinal constants or in the macro or microscopic appearance of the main organs.

No change was noted in the body weight pattern, and there was no mortality.

The administered doses are in fact greater than the scheduled human therapeutic doses.

The fetal toxicity test was carried out on 100 Sprague Dawley albino rats, 40 males and 60 females, having an average weight of 125 grams. Doses of 0, 25, 50 and 100 mg/kg of each examined compound were administered orally both to groups of 10 males, for a period of 60 days before copulation, and to groups of 20 females, for a period of 15 days before copulation.

For each examined product, the tests were also carried out on 40 adult rabbits of New Zealand White stock of average weight 3 kg. The products were administered orally at doses of 0, 20, 40, and 60 mg/kg from the 6th to the 18th day of pregnancy.

The fetal toxicity tests gave results which exclude any negative interference with the progress of pregnancy or with the conception products.

The administered doses are in fact greater than the scheduled human therapeutic doses.

All compounds from AU/001 to AU/020 as described in Table A were examined.

For each examined compound, the test for evaluating cardiocirculatory effects was carried out on 6 male rabbits of New Zealand White stock having a weight of about 2.5 kg, and anesthetised by means of ethyl urethane, using doses of 100 mg/kg in the case of oral administration (3 animals) and 20 mg/kg in the case of intravenous administration (3 animals).

No change was noted in arterial pressure, in respiration amplitude or frequency, or in the electrocardiograph trace. All compounds from AU/001 to AU/020 as described in Table A were examined.

To study the effect of the new compounds according to the present invention, 50 male and female rats of Sprague Dawley stock weighing approximately 200 grams were used for each compound examined.

The animals, under diet, were subjected to legature of the pylorus.

One hour after this operation, the animals were treated orally either with doses of 1, 3, 10 and 30 mg/kg of the examined compounds, or with doses of 3, 10, 30 and 100 mg/kg of cimetidine, or with doses of 1, 3, 10 and 30 mg/kg of ranitidine.

The administration of the compounds according to the present invention, of cimetidine and of ranitidine all significantly inhibit the incidence of gastric ulcers induced by the ligature of the pylorus.

The activity of the examined compounds according to the present invention is approximately 3 times that of cimetidine, and 1.2–1.3 times that of ranitidine. All compounds from AU/001 to AU/020 as described in Table A were examined.

In order to study the effect of the new compounds according to the invention on ulcers induced by retention, 60 male albino rats of Sprague-Dawley stock, of approximate weight 200 grams, were used for each compound examined. One group of animals received only the vehicle and served as the control group. Two experimental groups were pretreated orally with the examined compounds at doses of 3 and 10 mg/kg.

Before being placed in the retention cages, a further two groups received cimetidine orally at doses of 10 and 20 mg/kg. Finally, before being placed in the retention cages, a further two groups received ranitidine orally at doses of 3 and 10 mg/kg.

The incidence of gastric ulcers induced experimentally by cold retention was reduced by administering the new compounds according to the invention to a more marked degree than that observed with doses of cimetidine which were 3.3 times greater and with doses of ranitidine which were 1.1–1.2 times greater. All compounds from AU/001 to AU/020 as described in Table A were examined.

In order to study the curative effect of the new compounds according to the invention on ulcers induced by retention, 30 male albino rats of Sprague-Dawley stock with an average weight of 200 grams were used for each product examined.

The animals, which had fasted for 16 hours, were placed in retention cages for a period of 24 hours at a temperature of 21° C.

They were then freed, and treated with the products for a maximum period of 15 days in accordance with the following scheme:

1st group:
  controls sacrificed after 5 days (5 animals) and after 15 days (5 animals)
2nd group:
  compounds examined: 2.5 mg/kg by oral administration, sacrificed after 5 days (5 animals) and after 15 days (5 animals)
3rd group:
  compounds examined: 5 mg/kg by oral administration, sacrificed after 5 days (5 animals) and after 15 days (5 animals).

Repeated administration of the examined compounds favours cicatrisation of ulcers induced by retention. All compounds from AU/001 to AU/020 described in Table A were examined.

The new compounds according to the present invention, indicated by the symbols AU/001 to AU/020 in Table A, and administered orally in doses of 0.25 and 0.50 mg/kg and intravenously in doses of 0.10 and 0.20 mg/kg to male albino rats of Sprague-Dawley stock significantly reduce the volume of gastric secretion and gastric acidity, without causing alteration of the pH of the gastric juices.

In studying the effect of the new compounds according to the invention on gastric hyperacidity induced by tetragastrin, 30 male albino rats of Sprague-Dawley stock with an average weight of 180 grams were used for each compound examined.

The animals, fasting for 16 hours, were kept under anesthesia by ethyl urethane. A cannula was inserted into the stomach of the animals for collecting the gastric secretion in accordance with the method of Ishii and Shinoraki, Jap. J. Pharmacol. 18, 93–1968, after ligature of the pylorus and the cervical region of the esophagus.

The animals prepared in this manner received tetragastrin at a dose of 0.5 mg/kg by subcutaneous administration.

Simultaneously with the tetragastrin administration, the animals were treated either with a physiological solution (controls) or with the examined compounds by intravenous injection, at doses of 0.25 mg and 0.50 mg/kg.

The hyperacidity induced by the tetragastrin administration was significantly inhibited by the intravenous treatment with the examined compounds. All compounds from AU/001 to AU/020 described in Table A were examined.

Because of their high activity and practical absence of side effects, the compounds of formula (I) and their pharmaceutically acceptable salts are particularly useful as active principles in the formulation of pharmaceutical compounds. Consequently, the present invention also relates to pharmaceutical compounds characterised by containing as their active principal an effective quantity of one or more compounds of formula (I) or their pharmaceutically acceptable salts, either as such or in union with other compatible active principles, and/or with vehicles, diluents, solvents and/or pharmaceutically acceptable excipients.

Said pharmaceutical compositions can be formulated for administration orally, rectally, by injection or topically. They can for example be of solid form such as capsules, tablets, sustained-release tablets, single dosage sachets, suppositories or ointments, or in liquid form as solutions, suspensions or emulsions, for use either as such or for extemporaneous preparation. All the aforesaid pharmaecutical compounds can be formulated to contain diluents, vehicles, solvents and/or excipients well known to the art, and can be prepared by the methods well known to the art, fully described for example in "Tecnologia Farmaceutica", Silvano Casadio—Publ. Cisalpino Goliardica—Milan 1972.

The new compounds according to the present invention can be administered either as such or in the form of pharmaceutically acceptable salts, in quantities from 0.2 to 50 mg/kg per day, and preferably from 0.5 to 20 mg/kg per day, and advantageously in stepped doses such as from 2 to 4 times per day in posological units which contain for example 10, 20, 30, 50, 100, 200, 250, 500 mg of active principle.

The present invention also relates to the preparation of compounds of formula (I) and their pharmaceutically acceptable salts, which can be effected by reacting 2-[[[5-[(dimethlyamino)methyl]-2-furanyl]methyl]thio]ethylmethylsulphide of formula (III)

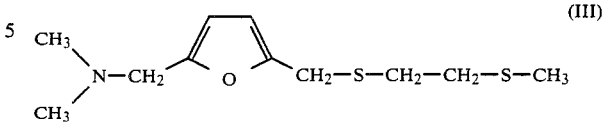

with a compound of formula (II)

in which R is as heretofore defined, at a temperature of 80° C., then isolating the compound of formula (I) obtained, then optionally salifying it.

Advantageously, an excess of the compound of formula (III) is used, and the reaction is carried out in 3 hours.

The compound of formula (II) can be prepared, according to a further subject matter of the present invention, by reacting 1,1-bis-(methylthio)-2-nitroethylene of formula (IV)

with a compound of formula (V)

in which R is as heretofore defined, and then with ammonia.

This reaction can be usefully carried out in organic solvents, advantageously tetrachloroethane.

The product obtained can be purified by passing it through a column of silica gel, followed by crystallisation.

The compound of formula (III) can be prepared by the process described in Italian patent application 19473A/82 filed in the name of the same applicant.

The obtained compounds of formula (I) can be easily isolated by the well known methods of the art, for example by crystallisation from solvents. Advantageously, these solvents are a water-ethyl alcohol mixture.

The optional salification can also be conducted by the methods known to the art, for example by adding the suitable acid.

The following examples illustrate some embodiments of the present invention, but without limiting it in any way.

EXAMPLE 1

1-N-[2-[[5-[(dimethylamino)methyl]furfuryl]thio]ethyl-]amino-1-piperidino-2-nitro-ethene (AU/001)

24.54 grams of 2-[[5-[(dimethylamino)methyl]furfuryl]thio]ethylmethylsulphide are reacted with 35 grams of 1-amino-1-piperidino-2-nitroethene at 80° C. for 3 hours. The mixture is cooled and taken up in ethyl ether. It is filtered, the precipitate is dissolved in ethyl alcohol and reprecipitated with water. The product is crystallised with a mixture of water and ethyl alcohol.

The product melts at 101°–105° C. Spectrophotometric analyses confirm its structure.

| Elementary analysis C$_{17}$H$_{28}$N$_4$O$_3$S | | Molecular weight 368.481 | |
|---|---|---|---|
| | C | H | N | S |
| calculated | 55.51% | 7.66% | 15.21% | 8.70% |
| found | 55.8% | 7.5% | 15.2% | 8.60% |

EXAMPLE 2

1-N-[2-[[5-[(dimethylamino)methyl]furfuryl]thio]ethyl]amino-1-(4-methyl-piperidino)-2-nitro-ethene (AU/002)

24.54 grams of 2-[[5-[(dimethylamino)methyl]furfuryl]thio]ethylmethylsulphide are reacted with 37 grams of 1-amino-1-(4-methyl-piperidino)-2-nitroethene at 80° C. for 3 hours. It is cooled and the procedure described in Example 1 is followed. The product melts at 105°–110° C. Spectrophotometric analyses confirm its structure.

| Elementary analysis C$_{18}$H$_{30}$N$_4$O$_3$S | | Molecular weight 382.508 | |
|---|---|---|---|
| | C | H | N | S |
| calculated | 56.52% | 7.91% | 14.65% | 8.38% |
| found | 57% | 7.90% | 15% | 8.35% |

EXAMPLE 3

N-[2-[[5-[(dimethylamino)methyl]furfuryl]thio]ethyl]-N'-(N-ethylpiperidinyl)-2-nitro-1,1-ethenediamine (AU/003)

24.54 grams of 2-[[5-[(dimethylamino)methyl]furfuryl]thio]ethylmethylsulphide are reacted with 40 grams of 2-nitro-N-(N-ethylpiperidinyl)-1,1-ethenediamine at 80° C. for 3 hours. The mixture is cooled and the procedure described in Example 1 is followed. The product melts at 95°–98° C.; spectrophotometric analyses confirm its structure.

| Elementary analysis C$_{19}$H$_{32}$N$_5$SO$_3$ | | Molecular weight 410.57 | |
|---|---|---|---|
| | C | H | N | S |
| calculated | 55.58% | 7.86% | 17.06% | 7.81% |
| found | 55.6% | 7.85% | 17.1% | 7.82% |

EXAMPLE 4

1-N-[2-[[5-[(dimethylamino)methyl]furfuryl]thio]ethyl]-amino-1-4-(2-hydroxyethyl)-1-piperazino ethene (AU/004)

24.54 grams of 2-[[5-[(dimethylamino)methyl]furfuryl]thio]ethylmethylsulphide are reacted with 43 grams of 1-amino-1-[4-(2-hydroxyethyl)-piperazino]-2-nitroethene at 80° C. for 3 hours. The mixture is cooled and the procedure described in Example 1 is followed. The product melts at 95°–101° C. Spectrophotomethic analyses confirm its structure.

| Elementary analysis C$_{18}$H$_{31}$N$_5$SO$_4$ | | Molecular weight 413.55 | |
|---|---|---|---|
| | C | H | N | S |
| calculated | 52.28% | 7.56% | 16.92% | 7.75% |
| found | 52.3% | 7.6% | 17% | 7.8% |

EXAMPLE 5

1-N-[2-[[5-[(dimethylamino)methyl]furfuryl]thio]ethyl]-amino-1-(4-benzyl-piperidino)-2-nitroethene (AU/005)

24.54 grams of 2-[[5-[(dimethylamino)methyl]furfuryl]thio]ethylmethylsulphide are reacted with 52 grams of 1-amino-1-(4-benzyl-piperidino)-2-nitroethene at 80° C. for 3 hours. The mixture is cooled and the procedure described in Example 1 is followed. The product melts at 102°–106° C. Spectrophotometric analyses confirm its structure.

| Elementary analysis C$_{24}$H$_{34}$N$_4$SO$_3$ | | Molecular weight 458.64 | |
|---|---|---|---|
| | C | H | N | S |
| calculated | 62.85% | 7.47% | 12.22% | 6.99% |
| found | 63% | 7.5% | 12.3% | 7% |

EXAMPLE 6

1-N-[2-[[5-[(dimethylamino)methyl]furfuryl]thio]ethyl]-amino-1-(4-benzyl-piperazino)-2-nitroethene (Au/006)

24.54 grams of 2-[[5-[(dimethylamino)methyl]furfuryl)]thio]ethylmethylsulphide are reacted with 53 grams of 1-amino-1-(4-benzyl-1-piperazino)-2-nitroethene at 80° C. for 3 hours. The mixture is cooled and the procedure described in Example 1 is followed. The product melts at 104°–108° C. Spectrophotometric analyses confirm its structure.

| Elementary analysis C$_{23}$H$_{33}$N$_5$SO$_3$ | | Molecular weight 459.61 | |
|---|---|---|---|
| | C | H | N | S |
| calculated | 60.11% | 7.24% | 15.24% | 6.98% |
| found | 60% | 7.2% | 13.3% | 7% |

EXAMPLE 7

1-N-[2-[[5-[(dimethylamino)methyl]furfuryl]thio]ethyl]-amino-1-ethyleneimino-2-nitroethene (AU/007)

24.54 grams of 2-[[5-[(dimethylamino)methyl]furfuryl]thio]ethylmethylsulphide are reacted with 26 grams of 1-amino-1-ethyleneimino-2-nitroethene at 80° C. for 3 hours. The mixture is cooled and the procedure described in Example 1 is followed. The product melts at 107°–110° C. Spectrophotometric analyses confirm its structure.

| Elementary analysis C$_{14}$H$_{22}$N$_4$SO$_3$ | | Molecular weight 326.46 | |
|---|---|---|---|
| | C | H | N | S |
| calculated | 51.51% | 6.79% | 17.16% | 9.82% |
| found | 51.6% | 6.8% | 17.2% | 9.8% |

EXAMPLE 8

1-N-[2-[[5-[(dimethylamino)methyl]furfuryl]thio]ethyl]-amino-1-cyclopropyleneimino-2-nitroethene (AU/008)

24.54 grams of 2-[[5-[(dimethylamino)methyl]furfuryl]thio]ethylmethylsulphide are reacted with 31 grams of 1-amino-1-cyclopropyleneimino-2-nitroethene at 80° C. for 3 hours. The mixture is cooled and the procedure described in Example 1 is followed. The product melts at 106°–109° C. Spectrophotometric analyses confirm its structure.

| Elementary analysis C$_{15}$H$_{24}$N$_4$SO$_3$ | Molecular weight 340.46 | | |
|---|---|---|---|
| | C | H | N | S |
| calculated | 52.33% | 7.11% | 16.46% | 9.42% |
| found | 52.3% | 7.2% | 16.5% | 9.45% |

EXAMPLE 9

N-[2-[[5-[(dimethylamino)methyl]furfuryl]thio]ethyl]-N'-(cyclohexyl)-2-nitro-1,1-ethenediamine (AU/009)

24.54 grams of 2-[[5-[(dimethylamino)methyl]furfuryl]thio]ethylmethylsulphide are reacted with 37 grams of 2-nitro-N-cyclohexyl-1,1-ethenediamine at 80° C. for 3 hours. Th mixture is cooled and the procedure described in Example 1 is followed. The product melts at 97°–99° C. Spectrophotometric analyses confirm its structure.

| Elementary analysis C$_{18}$H$_{30}$N$_4$SO$_3$ | Molecular weight 382.53 | | |
|---|---|---|---|
| | C | H | N | S |
| calculated | 56.52% | 7.91% | 14.65% | 8.38% |
| found | 56.6% | 8% | 14.7% | 8.4% |

EXAMPLE 10

N-[2-[[5-[(dimethylamino)methyl]furfuryl]thio]ethyl]-N'-(1,4-ciclohexadienyl)-2-nitro-1,1-ethenediamine (AU/010)

24.54 grams of 2-[[5-[(dimethylamino)methyl]furfuryl]-2-thio]ethylmethylsulphide are reacted with 36 grams of 2-nitro-N-(1,4-cyclohexadienyl)-1,1-ethenediamine at 80° C. for 3 hours. The mixture is cooled and the procedure described in Example 1 is followed. The product melts at 103°–107° C. Spectrophotometric analyses confirm its structure.

| Elementary analysis C$_{18}$H$_{28}$N$_4$SO$_4$ | Molecular weight 380.53 | | |
|---|---|---|---|
| | C | H | N | S |
| calculated | 56.82% | 7.42% | 14.72% | 8.43% |
| found | 57% | 7.45% | 15% | 8.4% |

EXAMPLE 11

N-[2-[[5-[(dimethylamino)methyl]furfuryl]thio]ethyl]-N'-(1,4-cyclohexadienyl-2-methyl)-2-nitro-1,1-ethenediamine (AU/011)

24.54 grams of 2-[5-[(dimethylamino)methyl]furfuryl]thio]ethylmethylsulphide are reacted with 40 grams of 2-nitro-N'-(1,4-cyclohexadienyl-2-methyl)1,1-ethenediamine at 80° C. for 3 hours. The mixture is cooled and the procedure described in Example 1 is followed. The product melts at 99°–103° C. Spectrophotometric analyses confirm its structure.

| Elementary analysis C$_{19}$H$_{28}$N$_4$SO$_4$ | Molecular weight 386.52 | | |
|---|---|---|---|
| | C | H | N | S |
| calculated | 59.04% | 5.75% | 14.50% | 8.29% |
| found | 60% | 5.8% | 14.4% | 8.3% |

EXAMPLE 12

N-[2-[[5-[(dimethylamino)methyl]furfuryl]thio]ethyl]-N'-(1,4-cyclohexadienyl-2-ethyl)-2-nitro-1,1-ethenediamine (AU/012)

24.54 grams of 2-[[5-[(dimethylamino)methyl]furfuryl]thio]ethylmethylsulphide are reacted with 41 grams of 2-nitro-N'-(1,4-cyclohexadienyl-2-ethyl)-1,1-ethenediamine at 80° C. for 3 hours. The mixture is cooled and the procedure described in Example 1 is followed. Spectrophotometric analyses confirm the structure of the compound obtained.

| Elementary analysis C$_{20}$H$_{30}$N$_4$SO$_3$ | Molecular weight 406.55 | | |
|---|---|---|---|
| | C | H | N | S |
| calculated | 59.08% | 7.44% | 13.78% | 7.89% |
| found | 60% | 7.5% | 13.7% | 7.9% |

EXAMPLE 13

1-N-[2-[[5-[(dimethylamino)methyl]furfuryl]thio]ethyl]-amino-1-hexamethyleneimino-2-nitroethene (AU/013)

24.54 grams of 2-[[5-[(dimethylamino)methyl]furfuryl]thio]ethylmethylsulphide are reacted with 37 grams of 1-amino-1-(hexamethyleneimino)-ethene at 80° C. for 3 hours. The mixture is cooled and the procedure described in Example 1 is followed. Spectrophotometric analyses confirm the structure of the compound obtained.

| Elementary analysis C$_{18}$H$_{30}$N$_4$SO$_3$ | Molecular weight 382.56 | | |
|---|---|---|---|
| | C | H | N | S |
| calculated | 56.51% | 7.90% | 14.65% | 8.38% |
| found | 56.8% | 8% | 14.6% | 8.4% |

EXAMPLE 14

N-[2-[[5-[(dimethylamino)methyl]furfuryl]thio]ethyl]-N'-(hexamethyleneimino)-2-nitro-1,1-ethenediamine (AU/014)

24.54 grams of 2-[[5-[(dimethylamino)methyl]furfuryl]thio]ethylmethylsulphide are reacted with 40 grams of 2-nitro-N-hexamethyleneimino-1,1-ethenediamine at 80° C. for 3 hours. The mixture is cooled and the procedure described in Example 1 is followed. Spectrophotometric analyses confirm the structure of the compound obtained.

| Elementary analysis C$_{18}$H$_{31}$N$_5$SO$_3$ | Molecular weight 397.57 | | |
|---|---|---|---|
| | C | H | N | S |
| calculated | 54.38% | 7.86% | 17.62% | 8.06% |
| found | 55% | 7.9% | 17.7% | 8% |

EXAMPLE 15

N-[2-[[5-[(dimethylamino)methyl]furfuryl]thio]ethyl]-N'-cycloheptyl-2-nitro-1,1-ethenediamine (AU/015)

24.54 grams of 2-[[5-[(dimethylamino)methyl]furfuryl]thio]ethylmethyl sulphide are reacted with 40 grams of 2-nitro-N-cycloheptyl-1,1-ethenediamine at 80° C. for 3 hours. The mixture is cooled and the procedure described in Example 1 is followed. The product melts at 91°–94° C. Spectrophotometric analyses confirm its structure.

| Elementary analysis $C_{19}H_{33}N_4SO_3$ | | Molecular weight 397.56 | |
|---|---|---|---|
| C | H | N | S |
| calculated 57.40% | 8.37% | 14.09% | 8.06% |
| found 57.5% | 8.4% | 14.1% | 8.1% |

EXAMPLE 16

N-[2-[[5-[(dimethylamino)methyl]furfuryl]thio]ethyl]-N'-cyclopentyl-2-nitro-1,1-ethenediamine (AU/016)

24.54 grams of 2-[[5-[(dimethylamino)methyl]furfuryl]thio]ethylmethylsulphide are reacted with 42 grams of 2-nitro-N-cyclopentyl-1,1-ethenediamine at 80° C. for 3 hours. The mixture is cooled and the procedure described in Example 1 is followed. The product melts at 97°–103° C. Spectrophotometric analyses confirm its structure.

| Elementary analysis $C_{17}H_{28}N_4SO_3$ | | Molecular weight 369.46 | |
|---|---|---|---|
| C | H | N | S |
| calculated 55.27% | 7.64% | 15.17% | 8.68% |
| found 55.3% | 7.6% | 15.2% | 8.7% |

EXAMPLE 17

1-N-[2-[[5-[(dimethylamino)methyl]furfuryl]thio]ethyl]-amino-1-pyrrolidino-2-nitroethene (AU/017)

24.54 grams of 2-[[5-[(dimethylamino)methyl]furfuryl]thio]ethylmethylsulphide are reacted with 33 grams of 1-amino-1-pyrrolidino-2-nitroethene at 80° C. for 3 hours. The mixture is cooled and the procédure described in Example 1 is followed. The product melts at 95°–100° C. Spectrophotometric analyses confirm its structure.

| Elementary analysis $C_{16}H_{26}N_4SO_4$ | | Molecular weight 354.48 | |
|---|---|---|---|
| C | H | N | S |
| calculated 54.2% | 7.39% | 15.81% | 9.04% |
| found 54.1% | 7.4% | 15.8% | 9.1% |

EXAMPLE 18

1-N-[2-[[5-[(dimethylamino)methyl]furfuryl]thio]ethyl]-amino-1-morpholino-2-nitroethene (AU/018)

24.54 grams of 2-[[5-[(dimethylamino)methyl]furfuryl]thio]ethylmethylsulphide are reacted with 35 grams of 1-amino-1-morpholino-2-nitroethene at 80° C. for 3 hours. The mixture is cooled and the procedure described in Example 1 is followed. The product melts at 98°–103° C. Spectrophotometric analyses confirm its structure.

| Elementary analysis $C_{16}H_{26}N_4SO_4$ | | Molecular weight 370.45 | |
|---|---|---|---|
| C | H | N | S |
| calculated 51.88% | 7.08% | 15.12% | 8.65% |
| found 52% | 7.1% | 15.2% | 8.6% |

EXAMPLE 19

N-[2-[[5-[(dimethylamino)methyl]furfuryl]thio]ethyl]-N'-endo-2-norbonyl)-2-nitro-1,1-ethenediamine (AU/019)

24.54 grams of 2-[[5-[(dimethylamino)methyl]furfuryl]thio]ethylmethylsulphide are reacted with 40 grams of 2-nitro-N'-(endo-2-norbonyl)-1,1-ethenediamine at 80° C. for 3 hours. The mixture is cooled and the procedure described in Example 1 is followed. Spectrophotometric analyses confirm the structure of the compound obtained. Melting point 95°–100° C.

| Elementary analysis $C_{19}H_{30}N_4SO_3$ | | Molecular weight 394.54 | |
|---|---|---|---|
| C | H | N | S |
| calculated 57.84% | 7.66% | 14.28% | 8.13% |
| found 57.9% | 7.65% | 14.3% | 8.1% |

EXAMPLE 20

N-[2-[[5-[(dimethylamino)methyl]furfuryl]thio]ethyl]-N'-norbonen-2-yl)-2-nitro-1,1-ethenediamine (AU/20)

24.54 grams of 2-[[5-[(dimethylamino)methyl]furfuryl]thio]ethylmethylsulphide are reacted with 40 grams of 2-nitro-N-(norbonen-2-yl)-1,1-ethenediamine at 80° C. for 3 hours. The mixture is cooled and the procedure described in Example 1 is followed. Spectrophotometric analyses confirm the structure of the compound obtained. Melting point 96°–101° C.

| Elementary analysis $C_{19}H_{28}N_4SO_3$ | | Molecular weight 392.53 | |
|---|---|---|---|
| C | H | N | S |
| calculated 58.14% | 7.18% | 14.28% | 8.17% |
| found 58.2% | 7.2% | 14.3% | 8.12% |

EXAMPLE 21

1-amino-1-piperidino-2-nitroethene 16.5 grams of 1,1-bis-(methylthio)-2-nitroethene are dissolved under hot conditions in 100 ml of tetrachloroethane, 8.5 grams of piperidine are added, the mixture is heated under reflux for 2 hours, is then cooled and anhydrous gaseous ammonia is added until saturated.

The mixture is agitated for 2 hours. The solvent is evaporated under vacuum and the product obtained is purified through a silica gel chromatograph column. It is eluted with petroleum ether and then with dichloroethane.

The product which separates is crystallised from diethylether, and melts at 121°–123° C.

EXAMPLE 22

1-amino-1-(4-methyl-piperidino)-2-nitroethene

The procedure described in Example 21 is followed, but 9.9 grams of 4-methyl-piperidine are used instead of the piperidine.

The product obtained melts at 125°–128° C.

EXAMPLE 23

N-(3-N-ethylpiperidinyl)-2-nitro-ethenediamine

The procedure described in Example 21 is followed, but 16.6 grams of 3-amino-N-ethylpiperidine are used instead of the piperidine.

The product obtained melts at 118°–120° C.

EXAMPLE 24

1-amino-1-[4-(2-hydroxyethyl)-piperazino]-2-nitroethene

The procedure described in Example 21 is followed, but using equimolecular quantities of 1,1-bis-(methylthio)-2-nitroethene and 4-(2-hydroxyethyl)-1-piperazine.
The product obtained melts at 125°–128° C.

EXAMPLE 25

1-amino-1-(4-benzylpiperidino)-2-nitroethene

The procedure described in Example 21 is followed, but using equimolecular quantities of 1,1-bis(methylthio)-2-nitroethene and 4-benzylpiperidine, and then saturating with ammonia.
The product obtained melts at 125°–128° C.

EXAMPLE 26

1-amino-1-(4-benzyl-1-piperazino)-2-nitroethene

The procedure described in Example 21 is followed, but using equimolecular quantities of 1,1-bis-(methylthio)-2-nitroethene and 4-benzyl-1-piperazine, and then saturating with ammonia.
The product obtained melts at 118°–121° C.

EXAMPLE 27

1-amino-1-ethyleneimino-2-nitroethene

The procedure described in Example 21 is followed, but using equimolecular quantities of 1,1-bis-(methylthio)-2-nitroethene and ethyleneimine, and then saturating with ammonia. The product obtained melts at 98°–100° C.

EXAMPLE 28

1-amino-1-cyclopropyleneimino-2-nitroethene

The procedure described in Example 21 is followed, but using equimolecular quantities of 1,1-bis-(methylthio)-2-nitroethene and cyclopropyleneimine, and then saturating with ammonia.
The product obtained melts at 111°–115° C.

EXAMPLE 29

N-cyclohexyl-2-nitro-1,1-ethenediamine

The procedure described in Example 21 is followed, but using equimolecular quantities of 1,1-bis-(methylthio)-2-nitroethene and cyclohexylamine, and then saturating with ammonia.
The product obtained melts at 115°–118° C.

EXAMPLE 30

N-(1,4-cyclohexadienyl)-2-nitro-1,1-ethenediamine

The procedure described in Example 21 is followed, but using equimolecular quantities of 1,1-bis-(methylthio)-2-nitroethene and 1,4-cyclohexadienylamine, and then saturating with ammonia.
The product obtained melts at 120°–125° C.

EXAMPLE 31

N-(1,4-cyclohexadienyl-2-methyl)-2-nitro-1,1-ethenediamine

The procedure described in Example 21 is followed, but using equimolecular quantities of 1,1-bis-(methylthio)-2-nitroethene and 1,4-cyclohexadienyl-2-methylamine, and then saturating with ammonia. The product obtained melts at 125°–128° C.

EXAMPLE 32

N-(1,4-cyclohexadienyl-2-ethyl)-2-nitro-1,1-ethenediamine

The procedure described in Example 21 is followed, but using equimolecular quantities of 1,1-bis-(methylthio)-2-nitroethene and 1,4-cyclohexadienyl-2-ethylamine, and then saturating with ammonia. The product obtained melts at 120°–125° C.

EXAMPLE 33

1-amino-1-hexamethyleneimino-2-nitroethene

The procedure described in Example 21 is followed, but using equimolecular quantities of 1,1-bis-(methylthio)-2-nitroethene and hexamethyleneimine, and then saturating with ammonia. The product obtained melts at 128°–132° C.

EXAMPLE 34

N-cycloheptyl-2-nitro-1,1-ethenediamine

The procedure described in Example 21 is followed, but using equimolecular quantities of 1,1-bis-methylthio)-2-nitroethene and cycloheptylamine, and then saturating with ammonia. The product obtained melts at 118°–125° C.

EXAMPLE 35

N-cyclopentyl-2-nitro-1,1-ethenediamine

The procedure described in Example 21 is followed, but using equimolecular quantities of 1,1-bis-(methylthio)-2-nitroethene and cyclopentylamine, and then saturating with ammonia. The product obtained melts at 117°–124° C.

EXAMPLE 36

1-amino-1-pyrrolidino-2-nitroethene

The procedure described in Example 21 is followed, but using equimolecular quantities of 1,1-bis-(methylthio)-2-nitroethene and pyrrolidine, and then saturating with ammonia. The product obtained melts at 120°–125° C.

EXAMPLE 37

1-amino-1-morpholino-2-nitroethene

The procedure described in Example 21 is followed, but using equimolecular quantities of 1,1-bis-(methylthio)-2-nitroethene and morpholine, and then saturating with ammonia. The product obtained melts at 120°–125° C.

EXAMPLE 38

N-(endo-2-norbornyl)-2-nitro-1,1-ethenediamine

The procedure described in Example 21 is followed, but using equimolecular quantities of 1,1-bis-(methylthio)-2-nitroethene and endo-2-norbornylamine and then saturating with ammonia. The product obtained melts at 130°–131° C.

EXAMPLE 39

N-(norbornen-2-yl)-2-nitro-1,1-ethenediamine

The procedure described in Example 21 is followed, but using equimolecular quantities of 1,1-bis-(methylthio)-2-nitroethene and norbornen-2-yl-amine and then saturating with ammonia. The product obtained melts at 128°–132° C.

EXAMPLE 40

N-hexamethyleneimino-2-nitro-1,1-ethenediamine

The procedure described in Example 21 is followed, but using equimolecular quantities of 1,1-bis-(methylthio)-2-nitroethene and N-amino-hexamethyleneimine, and then saturating with ammonia. The product obtained melts at 127°–131° C.

Although the invention has been described in detail with reference to certain specific embodiments, it is apparent to the expert of the art that certain changes and modifications can be made thereto without leaving the scope of the inventive idea.

I claim:

1. Compounds of formula (I)

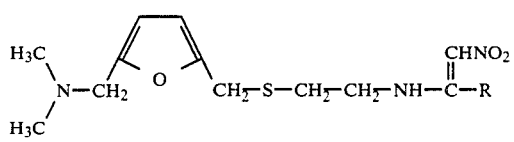

where R is a piperidino, 4-methylpiperidino, 4-benzyl-piperidino, ethyleneimino, cyclopropyleneimino, hexamethyleneimino, or pyrrolidino, or their pharmaceutically acceptable salts.

2. A compound as claimed in claim 1, characterised in that said pharmaceutically acceptable salt is the salt with hydrochloric, hydrobromic, hydroiodic, phosphoric, sulphuric, maleic, malic, acetic, citric, oxalic, succinic, benzoic, tartaric, fumaric, mandelic, ascorbic, methylsulphonic or ethylsulphonic acid.

3. A compound as claimed in claim 1, characterised by being 1-N-[2-[[5-[(dimethylamino)methyl]furfuryl]-thio]ethyl]-amino-1-piperidino-2-nitroethene.

4. A compound as claimed in claim 1, characterised by being 1-N-[2-[[5-[(dimethylamino)methyl]furfuryl]-thio]ethyl]-amino-1-(4-methyl-piperidino)-2-nitroethene.

5. A compound as claimed in claim 1, characterised by being 1-N-[2-[[5-[(dimethylamino)methyl]furfuryl]-thio]ethyl]-amino-1-(4-benzyl-piperidino)-2-nitroethene.

6. A compound as claimed in claim 1, characterised by being 1-N-[2-[[5-[(dimethylamino)methyl]furfuryl]-thio]ethyl]-amino-1-ethyleneimino-2-nitroethene.

7. A compound as claimed in claim 1, characterised by being 1-N-[2-[[5-(dimethylamino)methyl]furfuryl]-thio]ethyl]-amino-1-cyclopropyleneimino-2-nitroethene.

8. A compound as claimed in claim 1, characterised by being 1-N-[2-[[5-[(dimethylamino)methyl]furfuryl]-thio]ethyl]-amino-1-hexamethyleneimino-2-nitroethene.

9. A compound as claimed in claim 1, characterised by being 1-N-[2-[[5-[(dimethylamino)methyl]furfuryl]-thio]ethyl]-amino-1-pyrrolidino-2-nitroethene.

10. A compound characterised by being the pharmaceutically acceptable salt of a compound as claimed in one of claims 3, 4, 5, 6, 7, 8 or 9.

11. A pharmaceutical composition characterised by containing, as active principle, an effective quantity of one or more compounds as claimed in one of claims 1–4, 5, 6, 7, 8 or 9 in union with other compatible active principles and/or with vehicles, diluents, solvents, and/or pharmaceutically acceptable excipients.

12. A composition as claimed in claim 11, characterised by being suitable for oral, injectable, rectal or topical administration.

13. A composition as claimed in claim 12, characterised by being in tablet form.

14. A composition as claimed in claim 12, characterised by being in the form of a tablet of which the active principle is released in sustained manner.

15. A composition as claimed in claim 14, characterised in that each tablet contains between 20 and 500 mg of active principle.

16. A composition as claimed in claim 12, characterised by being in the form of a single dose sachet, a ready or extemporaneously prepared syrup, or an emulsion.

17. A composition as claimed in claim 12, characterised by being in the form of an oitment, cream or powder for topical application.

18. A composition as claimed in claim 17, characterised in that the content of the active principle can range from 0.5 to 10%.

* * * * *